(12) United States Patent
Ambatipudi

(10) Patent No.: US 9,827,236 B2
(45) Date of Patent: Nov. 28, 2017

(54) METHOD OF INHIBITING THE GLYCATION OF NUTRIENT AND ENDOGENOUS PROTEINS AND PEROXIDATION OF NUTRIENT AND ENDOGENOUS LIPIDS

(71) Applicant: Mythri Ambatipudi, San Jose, CA (US)

(72) Inventor: Mythri Ambatipudi, San Jose, CA (US)

(73) Assignee: Mythri Ambatipudi, San Jose, CA (US)

( * ) Notice: Subject to any disclaimer, the term of this patent is extended or adjusted under 35 U.S.C. 154(b) by 220 days.

(21) Appl. No.: 14/708,276

(22) Filed: May 10, 2015

(65) Prior Publication Data

US 2016/0324844 A1 Nov. 10, 2016

Related U.S. Application Data

(60) Provisional application No. 61/991,515, filed on May 11, 2014.

(51) Int. Cl.
*A61K 31/4172* (2006.01)
*A61K 31/455* (2006.01)
*A61K 31/375* (2006.01)
*A61K 31/05* (2006.01)
*A61K 31/352* (2006.01)
*A61K 31/353* (2006.01)
*A61K 31/355* (2006.01)
*A61K 38/05* (2006.01)
*A61K 45/06* (2006.01)
*A61K 31/7004* (2006.01)
*A61K 31/7016* (2006.01)

(52) U.S. Cl.
CPC ............ *A61K 31/455* (2013.01); *A61K 31/05* (2013.01); *A61K 31/352* (2013.01); *A61K 31/353* (2013.01); *A61K 31/355* (2013.01); *A61K 31/375* (2013.01); *A61K 31/4172* (2013.01); *A61K 31/7004* (2013.01); *A61K 31/7016* (2013.01); *A61K 38/05* (2013.01); *A61K 45/06* (2013.01)

(58) Field of Classification Search
CPC .. A61K 2300/00; A61K 31/05; A61K 31/352; A61K 31/353; A61K 31/355; A61K 31/375; A61K 31/4172; A61K 31/455; A61K 31/7004; A61K 31/7016; A61K 38/05; A61K 45/06
See application file for complete search history.

(56) References Cited

U.S. PATENT DOCUMENTS

| | | | | |
|---|---|---|---|---|
| 6,337,350 B1 * | 1/2002 | Rahbar | ............... | A61K 31/155 514/596 |
| 7,776,915 B2 * | 8/2010 | Morariu | ................. | A61K 8/41 424/401 |
| 8,343,517 B1 * | 1/2013 | Bezzek | .................. | A23L 33/16 424/400 |
| 2006/0251608 A1 * | 11/2006 | Wachsberg | ............. | A61K 8/02 424/74 |
| 2007/0014876 A1 * | 1/2007 | Shapira | ................. | A61K 31/00 424/682 |
| 2007/0060533 A1 * | 3/2007 | Yoshikawa | ............... | A23L 2/52 514/27 |
| 2011/0152371 A1 * | 6/2011 | Rupasinghe | ........ | A23D 7/0053 514/560 |
| 2015/0320096 A1 * | 11/2015 | Miranda-Massari | ... | A23L 33/00 424/489 |

OTHER PUBLICATIONS

Medilexicon. Definition of "endogenous". Accessed online at http://www.medilexicon.com/dictionary/29105 on Mar. 23, 2017, 2 pages.*

* cited by examiner

*Primary Examiner* — Marcela M Cordero Garcia
(74) *Attorney, Agent, or Firm* — Ingenium Patents LLC; Peter R. Kramer

(57) ABSTRACT

Methods for reducing the glycation of nutrient and endogenous proteins and methods for reducing the peroxidation of nutrient and endogenous lipids are provided herein. Several inhibitors and conditions of inhibiting glycation of nutrient and endogenous proteins and peroxidation of nutrient and endogenous lipids are also provided herein. Also provided are the methods for inhibiting and treating the conditions associated with the formation of glycated proteins, such as Alzheimer's disease, neuropathy, retinopathy and nephropathy and the methods for inhibiting and treating the conditions associated with the formation of peroxidized lipids, such as cancer and atherosclerosis.

10 Claims, 3 Drawing Sheets

Figure 1: Glycation of Proteins
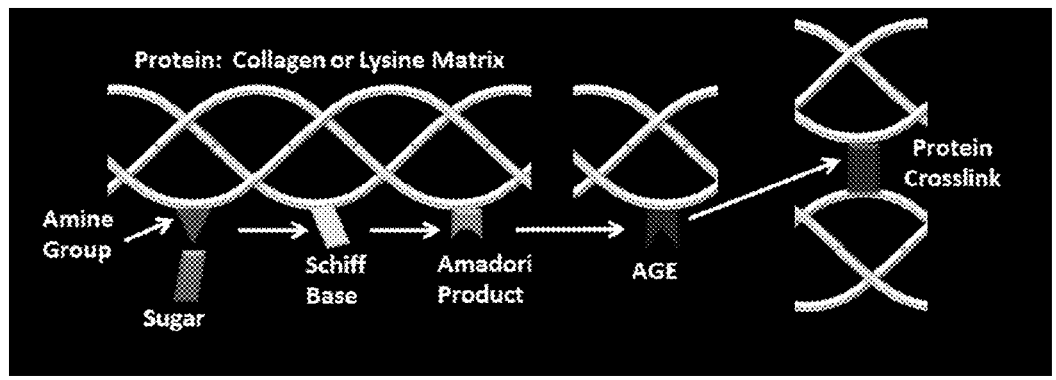
Figure 2: Peroxidation of Lipids
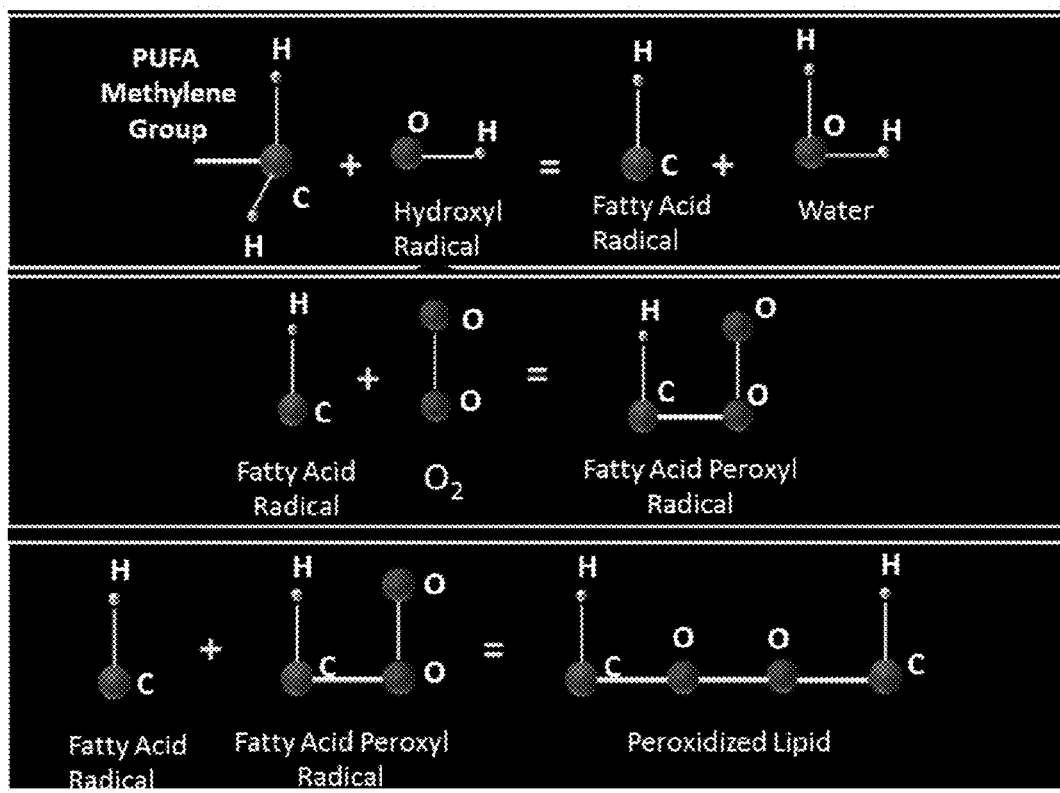

Figure 3: Inhibition of Nutrient Protein Glycation
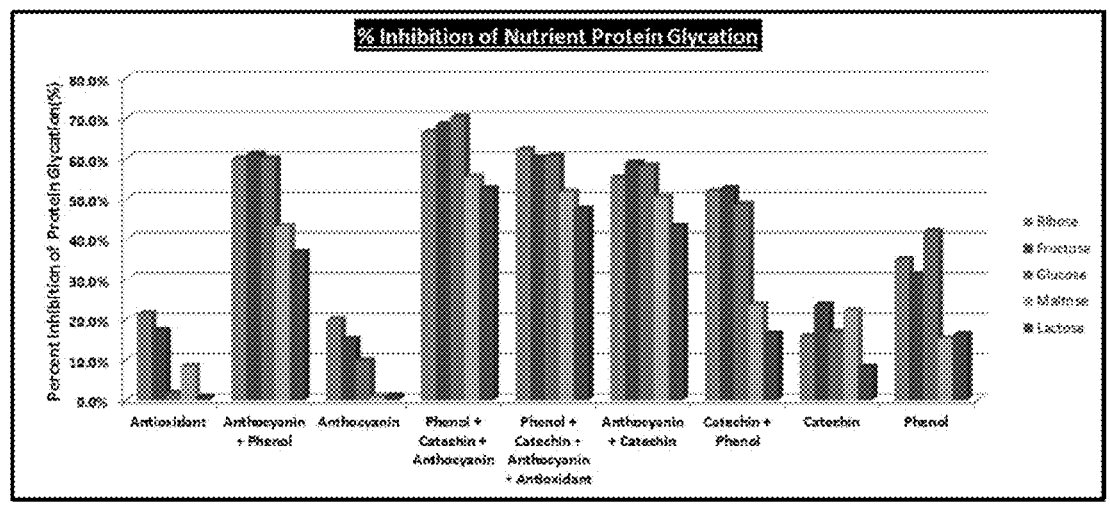
Figure 4: Inhibition of Endogenous Protein Glycation
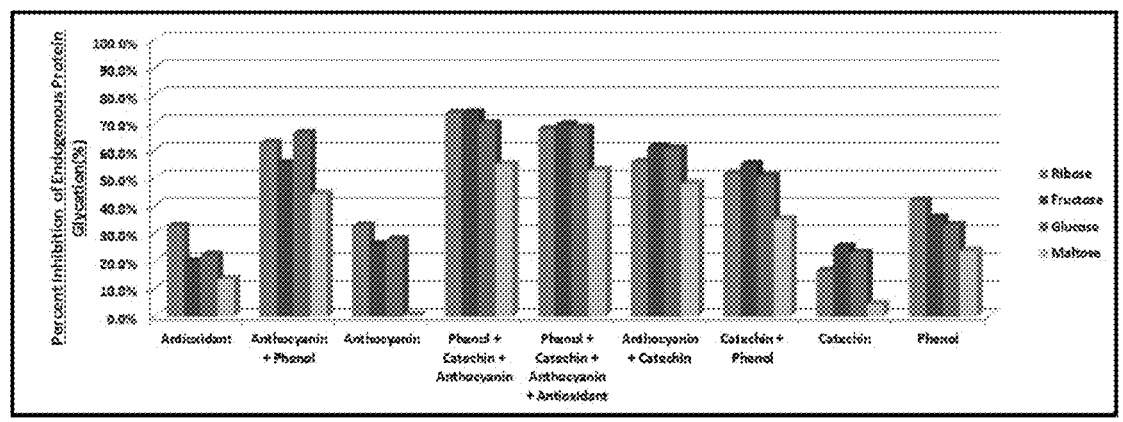

Figure 5: Inhibition of Nutrient Lipid Peroxidation with monounsaturated fatty acids (MUFA) or polyunsaturated fatty acid (PUFA) lipids
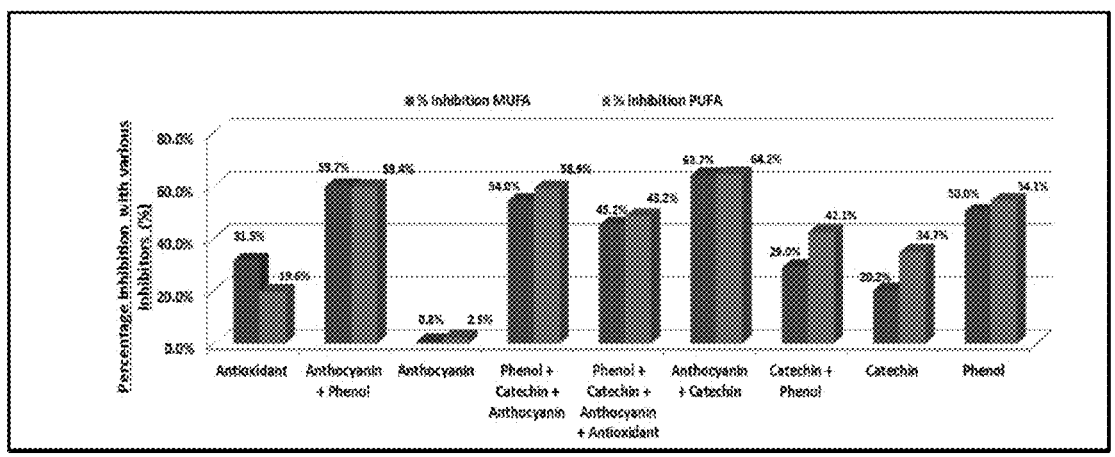
Figure 6: Inhibition of Endogenous Lipid Peroxidation with monounsaturated fatty acids (MUFA) or polyunsaturated fatty acid (PUFA) lipids
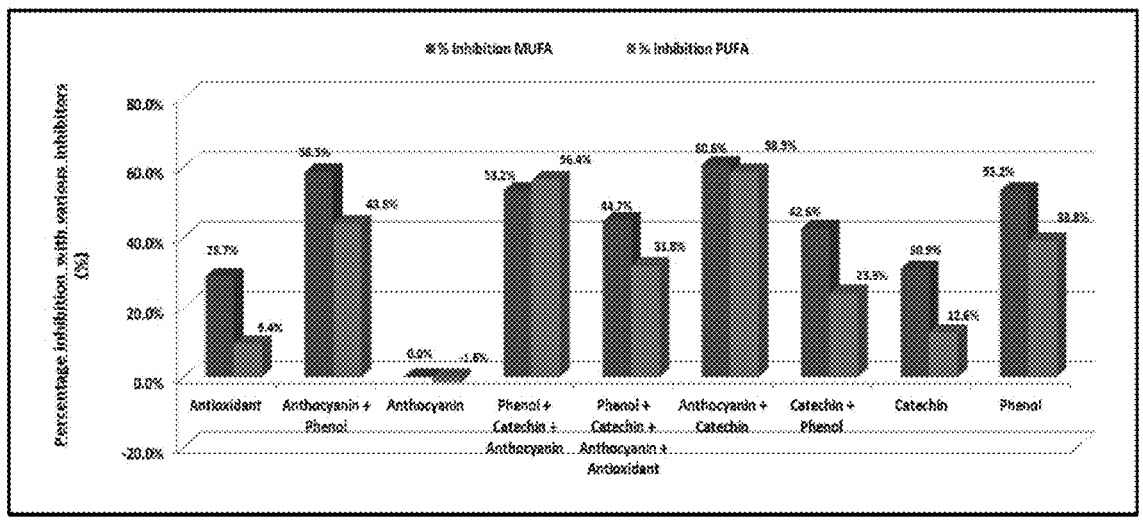

METHOD OF INHIBITING THE GLYCATION OF NUTRIENT AND ENDOGENOUS PROTEINS AND PEROXIDATION OF NUTRIENT AND ENDOGENOUS LIPIDS

1. FIELD OF THE INVENTION

This application relates to methods and compositions for reducing glycation in thermally processed nutrient proteins and endogenous proteins and for reducing peroxidation in thermally processed nutrient lipids and endogenous lipids. This application is also directed towards the methods for inhibiting and treating the conditions associated with the formation of glycated proteins, such as Alzheimer's disease, neuropathy, retinopathy and nephropathy. This application is also directed towards the methods for inhibiting and treating the conditions associated with the formation of peroxidized lipids, such as cancer and atherosclerosis.

2. BACKGROUND

Glycation of nutrient proteins and endogenous proteins in the presence of reducing sugars has been implicated in the pathogenesis of diseases such as Alzheimer's disease, neuropathy, nephropathy and retinopathy. Peroxidation of nutrient lipids and endogenous lipids has been implicated in the pathogenesis of diseases such as atherosclerosis and cancer. Together, glycated proteins and peroxidized lipids are called Advanced Glycation End-products (AGEs).

As shown in FIG. 1, amino acids/proteins react with reducing sugars to form glycated proteins. Cross links between proteins alters the proteins' structures and functions. Endogenously, this damages the extracellular matrix (ECM), basement membrane (BM) and smooth muscle tissue. Protein glycation also causing non-enzymatic browning in the nutrient proteins.

Protein glycation reactions are called Maillard Reaction. Here are the various stages of protein glycation:

In phase 1, schiff base is formed from the condensation of an amine group with the carbonyl group of a reducing sugar's aldehyde or ketone. The result is a Schiff base, an imine, in which C=O is replaced by C=N. An Amadori product is a re-arrangement from the Schiff base, in which the hydrogen atom from the OH adjacent to C=N moves to bond to nitrogen.

In phase 2, the Amadori products undergo any of these:
a. Dehydration forms reductones and dehydro reductones, which form carboxymethyl lysine and hydroxymethyl furfural.
b. Strecker degradation: Amadori products undergo enolization and deamination to produce dicarbonyls, which undergo decarboxilation and hydrolysis to produce a Strecker aldehyde.
c. Losing three water molecules and reacting with amino acids and water yields furfural and hydroxymethyl furfural.

In the third phase, phase 2 products react with amino acids to form melanoidins, precursors to the formation of glycated proteins.

FIG. 2 shows the oxidative degradation of lipids by reactive oxygen species (ROS). Here are the main steps of lipid peroxidation reactions.

Initiation: A fatty acid radical is produced. An ROS attacks the fatty acid, causing a hydrogen atom to be extracted from a methylene group. This generates fatty acid radicals.

Propagation:
a. The fatty acid radical reacts with molecular oxygen and produces a peroxyl-fatty acid radical.
b. The peroxyl-fatty acid radical reacts with a methylene group in the lipid and produces a lipid hydroperoxide and fatty acid radical.
c. The unstable lipid hydroperoxide breaks to produce alkoxy and a hydroxyl radical.
d. The alkoxy reacts with another methylene group and produces an alcohol and fatty acid radical.
e. These steps repeat.

Termination:
a. The fatty acid radical reacts with molecular oxygen and produces a peroxyl-fatty acid radical.
b. Two alkoxy radicals react to produce lipid peroxide.
c. A peroxyl-fatty acid radical reacts with a fatty acid radical to form lipid peroxide.
d. An alkoxy radical reacts with a fatty acid radical to produce ether.
e. Two peroxyl-fatty acid radicals react to produce lipid peroxide and molecular oxygen.

Methods for inhibiting glycation of nutrient and endogenous proteins and peroxidation of nutrient and endogenous lipids are needed to provide a cure for major diseases.

3. SUMMARY OF THE INVENTION

Methods are provided for inhibiting the glycation of nutrient and endogenous proteins.

In one embodiment, the glycation of nutrient protein in the presence of a reducing sugar is inhibited by combining with a natural or synthetic inhibiting agent and when the combination is thermally processed at a temperature of less than 60 degree Celsius in an alkaline environment.

In another embodiment, the glycation of endogenous protein in the presence of endogenous reducing sugars is inhibited by administering the inhibiting agent in the form of food consumption.

The reducing sugar can be one of or a combination of ribose, fructose, glucose, lactose and maltose.

The nutrient protein can be lysine and the endogenous protein can be collagen.

In another embodiment, the peroxidation of nutrient lipids is inhibited by combining with a natural or synthetic inhibiting agent and when the combination is thermally processed at a temperature of less than 60 degree Celsius in an acidic environment.

In another embodiment, the peroxidation of nutrient lipids is inhibited by administering the inhibiting agent in the form of food consumption.

The nutrient or endogenous lipid can be monounsaturated fatty acid or polyunsaturated fatty acid.

In yet another embodiment, simultaneous inhibition of glycation of nutrient proteins and peroxidation of nutrient lipids is achieved when nutrient proteins and nutrient lipids are thermally processed at a temperature of less than 60 degree Celsius with a natural or synthetic inhibiting agent.

The inhibiting agent can be one or a combination of a flavonoid, a chelating agent or an antioxidant.

In one embodiment, the flavonoid can be one of or a combination of a phenol, an anthocyanin, a catechin.

In another embodiment, the antioxidant can be one of or a combination of tocopherol, niacinamide or ascorbic acid.

In yet another embodiment, the chelating agent can be carnosine.

4. BRIEF DESCRIPTION OF THE DRAWINGS

FIG. 1 shows the step by step process of glycation of proteins.

FIG. 2 shows the step by step process of peroxidation of lipids.

FIG. 3 shows the percentage inhibition of nutrient protein glycation with various inhibiting agents and their combinations. Percentage inhibition was determined using an in vitro experiment. Lysine was used to simulate the nutrient protein.

FIG. 4 shows the percentage inhibition of endogenous protein glycation with various inhibiting agents and their combinations. Percentage inhibition was determined using an in vitro experiment. Collagen was used to simulate the endogenous protein.

FIG. 5 shows the percentage inhibition of nutrient lipid peroxidation with various inhibiting agents and their combinations. Percentage inhibition was determined using an in vitro experiment. Olive oil, a polyunsaturated fatty acid (PUFA) and safflower oil, a monounsaturated fatty acid (MUFA) were used to simulate nutrient lipids.

FIG. 6 shows the percentage inhibition of nutrient lipid peroxidation with various inhibiting agents and their combinations. Percentage inhibition was determined using an in vitro experiment. Olive oil, a polyunsaturated fatty acid (PUFA) and safflower oil, a monounsaturated fatty acid (MUFA) were used to simulate nutrient lipids.

5. DETAILED DESCRIPTION

Glycation of nutrient or endogenous proteins in the presence of reducing sugars can lead to Alzheimer's disease, neuropathy, nephropathy and retinopathy. The various phases of glycation of proteins are described in FIG. 1. Peroxidation of nutrient and endogenous lipids can lead to cancer and atherosclerosis. The various phases of peroxidation of lipids are described in FIG. 2. Described herein, among other things, are novel methods of inhibiting protein glycation and lipid peroxidation in thermally processed nutrient proteins and lipids as well as endogenous proteins and lipids using natural or synthetic inhibitors rich in different types of flavonoids, chelating agents and antioxidants and their combinations.

In one embodiment of the present application, glycation is induced in the nutrient proteins by combining them with different types of sugars and thermally processing the combination at various temperatures and with various levels of alkalinity. The processing is repeated by adding the identified glycation inhibitor. The nutrient protein in this case could be lysine or any other nutrient protein in liquid, semisolid or solid form.

In another embodiment, glycation is induced in endogenous proteins by combining them with different types of sugars and thermally processing the combination at 37 degree Celsius to simulate internal human body temperature. The processing is repeated by adding the identified glycation inhibitor. The endogenous protein in this case could be collagen or any other endogenous protein in liquid, semisolid or solid form.

In another embodiment, peroxidation is induced in nutrient lipids by thermally processing them at various temperatures and with various levels of alkalinity. The processing is repeated by adding the identified peroxidation inhibitor. The nutrient lipid in this case could be polyunsaturated fatty acid or monounsaturated fatty acid in liquid, semisolid or solid form.

In yet another embodiment, peroxidation is induced in endogenous lipids by thermally processing the lipid at 37 degree Celsius to simulate internal human body temperature. The processing is repeated by adding the identified peroxidation inhibitor. The endogenous lipid in this case could be polyunsaturated fatty acid or monounsaturated fatty acid in liquid, semisolid or solid form.

In the context of this invention, thermal processing implies heating the food at various temperatures using any method of cooking such as baking, roasting, frying, boiling, etc. However, as shown in table 2 and table 3, glycation of proteins and peroxidation of lipids is inhibited most when thermally processed at 60 degree Celsius. Also, as shown in tables 4 and 5, nutrient lipid peroxidation decreases and protein glycation increases with increasing alkalinity.

In the context of this invention, the inhibiting agent could be in a liquid, solid or semisolid form. The inhibiting agent could be combined with the nutrient protein or nutrient lipid during, before or after the thermal processing.

In the context of this invention, the inhibiting agent could be in a natural and more than 90% pure form or could be manufactured synthetically. The inhibiting agent could be a flavonoid, such as an anthocyanin, a phenol or a catechin. The inhibiting agent could be manufactured synthetically or extracted from fruits such as red-wine resveratrol, berries, green tea leaves, etc. The inhibiting agent could also be an antioxidant in natural or synthetic form, such as ascorbic acid, tocopherol or niacinamide. The inhibiting agent can also be a chelating agent in natural or synthetic form, such as carnosine.

In certain embodiments, several combinations of inhibitors are used.

The effectiveness of the inhibiting agents and their combinations were ascertained using a series of in vitro experiments with nutrient lysine or collage protein, various sugars, natural polyunsaturated fatty acids and monounsaturated fatty acids and natural, pure form of inhibiting agents in extract forms. Absorbance values, measured using a spectrophotometer, were used to determine and compare formation of glycated proteins. Industry standard iodometric titration was used to determine and compare peroxidation levels in lipids.

In the case of inhibition of nutrient protein glycation and nutrient lipid peroxidation for disease prevention, it is recommended that the amount of inhibiting agent to be combined with the nutrient protein or nutrient lipid be as shown in the Table 1. Further, a combination of such inhibiting agents could be applied to increase the effectiveness of inhibition.

In the case of inhibition of endogenous protein glycation and endogenous lipid peroxidation, the amount of inhibiting agent to be administered to a human subject and the amount that will be effective in conjunction with a particular method will vary, e.g., with the nature and severity of the disease disorder and the route by which the active ingredient is administered. The frequency and dosage will also vary according to factors specific for each subject, such as age, body, weight, response, and the past medical history of the subject. Effective doses may be extrapolated from dose-response curves derived from in vitro or animal model test systems. Suitable regiments can be selected by one skilled in the art by considering such factors and by following, for example, dosages reported in the literature and recommended in the Physician's Desk Reference (58th ed., 2004).

By glycation inhibiting agent, it is meant that the agent could be an antioxidant, such as ascorbic acid that competes with glucose in hemoglobin and protein amino groups. This action could reduce or inhibit excessive glycation of red blood cells and proteins. An antioxidant type of inhibiting agent, such as ascorbic acid, can bind to biological proteins modulating their activities.

By peroxidation inhibiting agent, it is meant that the agent could be an antioxidant such as L-Ascorbic acid (or Vitamin C or ascorbate). An antioxidant is a molecule that inhibits the oxidation of other molecules. Antioxidants could terminate these chain reactions by removing free radical intermediates, and inhibit other oxidation reactions. Antioxidants neutralize free radicals either by providing the extra electron needed to make the pair, or by breaking down the free radical molecule to render it harmless.

Also, oxidation of sugars leads to the increased formation of sugar degradation products, which show a higher reactivity towards proteins than the regular sugar products. Antioxidants could interfere with sugar oxidation. Inhibiting agents, which can be antioxidants such as alpha-tocopherol, can prevent the auto-oxidation of sugars and inhibit protein glycation.

Often metals catalyze many oxidation reactions in the human body. This property of chelating agents can be used to inhibit protein glycation and lipid peroxidation. By glycation and peroxidation inhibiting agent, it is also meant that the ability of certain chelating agents such as carnosine to reduce the formation of altered proteins (typically adducts of methylglyoxal) and enhance proteolysis of aberrant polypeptides. Carnosine reacts with copper and decreases its reactivity thereby decreasing ascorbate oxidation by copper. Iron catalyzes the reaction between lipids and hydrogen peroxide. Carnosine not only inhibits the Iron, but also, inactivates the hydroxyl radicals generated as a result of the reaction between Fe and $H_2O_2$ thereby inhibiting lipid peroxidation. These dual actions might provide a rationale for the use of carnosine in the treatment or prevention of diverse age-related conditions where energy metabolism or proteostasis are compromised.

By glycation and peroxidation inhibitor, it is also meant that certain flavonoids such as phenols derived from resveratrol, or anthocyanins could be used to inhibit glycation by suppressing the receptor for glycated end products, the RAGE. This will prevent the cell/tissue from undergoing any change in response to the glycation, thereby saving the cell/tissue from any damage due to glycation. Resveratrol may inhibit peroxidation by decreasing the ROS formation or by scavenging the ROS formed in vitro by auto-oxidation of sugars and/or oxidative degradation of Amadori products. Phenols such as resveratrol could be used to inhibit lipid peroxidation mainly by scavenging lipid peroxyl radicals within the membrane.

TABLE 1

Concentration of inhibiting agent needed for 50% inhibition of nutrient protein glycation and nutrient lipid peroxidation

| | Concentration needed for 50% inhibition | |
|---|---|---|
| Inhibitor | Protein Glycation | Lipid Peroxidation |
| Phenol (Resveratrol) | 10% | 8% |
| Anthocyanin (Raspberry) | 22% | 17% |
| Catechin (EGCG) | 13% | 9% |

TABLE 1-continued

Concentration of inhibiting agent needed for 50% inhibition of nutrient protein glycation and nutrient lipid peroxidation

| | Concentration needed for 50% inhibition | |
|---|---|---|
| Inhibitor | Protein Glycation | Lipid Peroxidation |
| Chelating agent (Carnosine) | 16% | 12% |
| Antioxidant (Ascorbic Acid) | 7% | 11% |
| Antioxidant (Niacinamide) | 15% | 13% |
| Antioxidant (Tocopherol) | 17% | 15% |
| Anthocyanin (Strawberry) | 21% | 23% |

TABLE 2

Effect of temperature on protein glycation measured in in vitro experiment using a spectrophotometer

| | Absorbance at different temperatures | | | % decrease in AGE formation from |
|---|---|---|---|---|
| Sugar | 100 deg C. | 80 deg C. | 60 deg C. | 100 to 60 deg C. |
| Ribose | 0.59 | 0.52 | 0.13 | 78.1% |
| Fructose | 0.5 | 0.37 | 0.1 | 79.1% |
| Glucose | 0.47 | 0.34 | 0.1 | 77.6% |
| Maltose | 0.22 | 0.22 | 0.04 | 80.0% |
| Lactose | 0.17 | 0.18 | 0.06 | 67.9% |

TABLE 3

Effect of temperature on the generation of peroxide values measured in in vitro experiment using industry standard iodometric titration

| | Average Peroxide Value at different temperatures | | | % decrease in AGE formation from |
|---|---|---|---|---|
| Lipid | 100 deg C. | 80 deg C. | 60 deg C. | 100 to 60 deg C. |
| PUFA | 19.31 | 17.38 | 13.41 | 30.5% |
| MUFA | 5.04 | 4.58 | 3.48 | 31.0% |

TABLE 4

Effect of pH variation on protein glycation measured in an in vitro experiment using a spectrophotometer

| | Absorbance at different pH values | | | % decrease om AGE formation |
|---|---|---|---|---|
| Sugar | ph 4 | pH 8 | pH 10 | with decreasing pH |
| Ribose | 0.09 | 0.59 | 0.79 | 88.4% |
| Fructose | 0.07 | 0.5 | 0.65 | 89.4% |
| Glucose | 0.04 | 0.47 | 0.45 | 90.0% |
| Maltose | 0.04 | 0.22 | 0.26 | 84.4% |
| Lactose | 0.02 | 0.17 | 0.22 | 90.8% |

TABLE 5

Effect of pH variation on lipid peroxidation measured in an in vitro experiment using a spectrophotometer

| | Average Peroxide Value with varying pH | | | % Increase in AGE formation |
|---|---|---|---|---|
| Lipid | pH 4 | pH 8 | pH 10 | at lower pH |
| PUFA | 19.31 | 11.08 | 10.06 | 47.9% |
| MUFA | 5.04 | 3.42 | 1.86 | 63.1% |

PRIOR ART

| Patent # | Filing Date | Publication Date | Applicant | Title |
|---|---|---|---|---|
| WO2000059875A2 | Apr. 5, 2000 | Oct. 12, 2000 | Hope City | Novel inhibitors of formation of advanced glycation endproducts (age's) |
| US20070060533 A1 | Oct. 19, 2004 | May 6, 2005 | Meiji Seika Kaisha, Ltd | Novel inhibitor of the formation of advanced glycation end product and aldose reductase inhibitor |

The invention claimed is:

1. A method of inhibiting the glycation of a nutrient protein comprising,
   providing the nutrient protein with,
      a flavonoid, said flavonoid selected from the group consisting of anthocyanin and catechin,
      an antioxidant, said antioxidant selected from the group consisting of α-tocopherol, niacinamide, and ascorbic acid,
      and carnosine,
   thermally processing said nutrient protein at a temperature of less than 60 degrees Celsius in an alkaline environment.

2. The method of claim 1 wherein the flavonoid is anthocyanin.

3. The method of claim 2 wherein the antioxidant is niacinamide.

4. The method of claim 1 wherein the flavonoid is catechin.

5. The method of claim 4 wherein the antioxidant is niacinamide.

6. A method of inhibiting the peroxidation of nutrient lipid comprising,
   providing the nutrient lipid with,
      a flavonoid, said flavonoid selected from the group consisting of anthocyanin and catechin,
      an antioxidant, said antioxidant selected from the group consisting of α-tocopherol, niacinamide, and ascorbic acid,
      and carnosine,
   thermally processing said nutrient protein at a temperature of less than 60 degrees Celsius in an alkaline environment.

7. The method of claim 1 wherein the flavonoid is anthocyanin.

8. The method of claim 7 wherein the antioxidant is niacinamide.

9. The method of claim 1 wherein the flavonoid is catechin.

10. The method of claim 9 wherein the antioxidant is niacinamide.

\* \* \* \* \*